US010215982B2

(12) United States Patent
Britton

(10) Patent No.: US 10,215,982 B2
(45) Date of Patent: Feb. 26, 2019

(54) AIR CURTAIN GENERATOR FOR OPTICAL SENSING DEVICES

(71) Applicant: Halliburton Energy Services, Inc., Houston, TX (US)

(72) Inventor: Charles Cutler Britton, Houston, TX (US)

(73) Assignee: HALLIBURTON ENERGY SERVICES, INC., Houston, TX (US)

(*) Notice: Subject to any disclaimer, the term of this patent is extended or adjusted under 35 U.S.C. 154(b) by 0 days.

(21) Appl. No.: 15/703,602

(22) Filed: Sep. 13, 2017

(65) Prior Publication Data
US 2018/0003958 A1 Jan. 4, 2018

Related U.S. Application Data

(62) Division of application No. 15/023,487, filed as application No. PCT/US2013/702432 on Nov. 27, 2013, now abandoned.

(51) Int. Cl.
G02B 27/00 (2006.01)
B08B 17/02 (2006.01)
E21B 21/06 (2006.01)
E21B 47/01 (2012.01)
E21B 49/00 (2006.01)
G01N 21/15 (2006.01)

(52) U.S. Cl.
CPC .......... *G02B 27/0006* (2013.01); *B08B 17/02* (2013.01); *E21B 21/065* (2013.01); *E21B 47/011* (2013.01); *E21B 49/005* (2013.01); *G01N 21/15* (2013.01); *G01N 2021/151* (2013.01)

(58) Field of Classification Search
CPC ..... G02B 27/006; B08B 17/02; E21B 21/065; E21B 47/011; E21B 49/005; G01N 21/15
USPC ......................................... 359/507, 509, 900
See application file for complete search history.

(56) References Cited

U.S. PATENT DOCUMENTS

| 897,290 A | 9/1908 | Jacobs |
| 2,353,258 A | 7/1944 | Mott |
| 2,428,630 A | 10/1947 | Lanter |
| 2,850,005 A | 9/1958 | Good et al. |
| 2,896,854 A * | 7/1959 | Noble ...................... F23M 7/00 235/132 R |
| 3,469,088 A | 9/1969 | Coleman et al. |
| 7,417,749 B1 | 8/2008 | Simpson et al. |
| 2006/0068696 A1 | 3/2006 | Ashford et al. |
| 2007/0097454 A1 | 5/2007 | Kim |

(Continued)

FOREIGN PATENT DOCUMENTS

WO  WO 2013/089683  6/2013

OTHER PUBLICATIONS

Office Action issued for Canadian Patent Application No. 2,924,993 dated Sep. 25, 2017.

(Continued)

*Primary Examiner* — Ricky D Shafer

(57) ABSTRACT

A disclosed example of a sensing device includes an optical surface and an air curtain generator positioned around the optical surface. The air curtain generator has at least one nozzle operable to provide a continuous forced air region traveling away from the optical surface, thereby forming an air curtain around the optical surface that provides a debris barrier for the optical surface.

19 Claims, 4 Drawing Sheets

(56) References Cited

U.S. PATENT DOCUMENTS

2008/0285132 A1   11/2008  O'Kane
2010/0282647 A1   11/2010  Miller et al.
2011/0023915 A1    2/2011  McConnell
2012/0030901 A1    2/2012  Manninen et al.

OTHER PUBLICATIONS

International Search Report, dated Aug. 22, 2014, PCT/US2013/072432, 3 pages, ISA/KR.

* cited by examiner

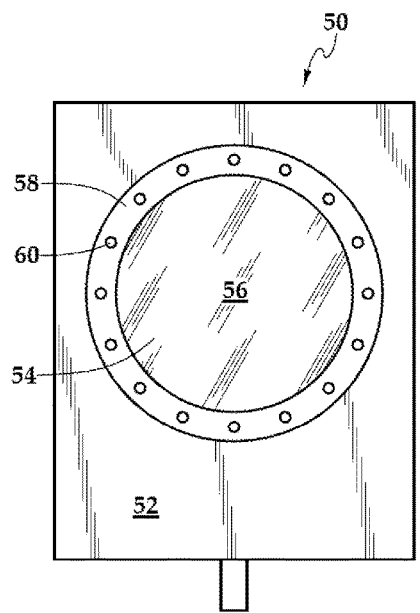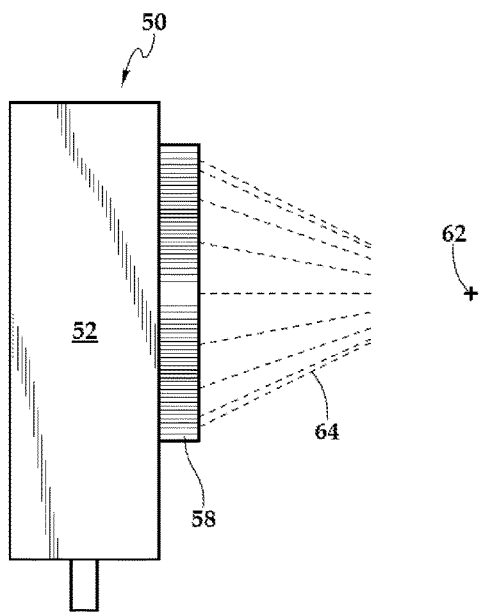
*Fig.2A*  *Fig.2B*
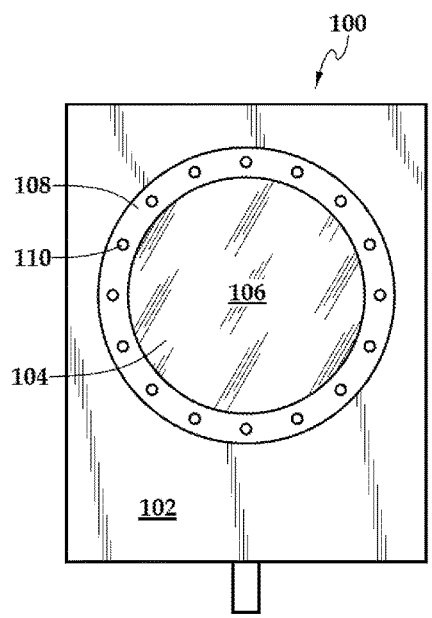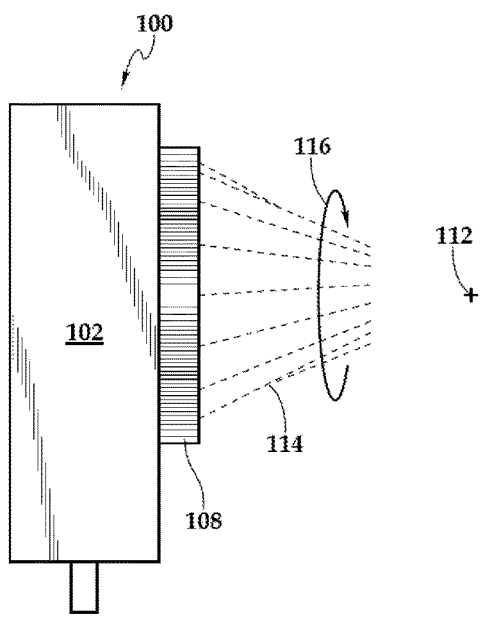
*Fig.3A*  *Fig.3B*

AIR CURTAIN GENERATOR FOR OPTICAL SENSING DEVICES

PRIORITY

The present application is a Divisional application of U.S. patent application Ser. No. 15/023,487, filed on Mar. 21, 2016, which is a U.S. National Stage patent application of International Patent Application No. PCT/US2013/072432, filed on Nov. 27, 2013, the benefits of which are claimed and the disclosures of which are incorporated herein by reference in their entirety.

TECHNICAL FIELD OF THE DISCLOSURE

This disclosure relates, in general, to equipment used in conjunction with sensing devices operated in an air environment and, in particular, to an air curtain generator for creating a debris barrier that protects an optical surface of a sensing device.

BACKGROUND

Without limiting the scope of the present disclosure, its background is described with reference, by way of example, to sensing devices operated in the hydrocarbon well drilling industry.

It is well known in the subterranean well drilling art to circulate mud downhole during drilling activity to cool the drill bit and to carry the drill cuttings back to the surface. In a typical mud system, the mud is circulated in a loop. For example, the mud may be pumped from a mud tank downhole to the drill bit then up the annulus to the surface. The mud is then returned to the mud tank for recirculation after removal of the drill cuttings and other solid particles or fines. In general, one step of solids removal may involve passing the mud through an inclined shaker that separates a majority of the drill cuttings from the mud. The mud passes through a shaker screen while the drill cuttings progress across the top of the shaker screen in the direction of the incline.

Information relating to the well and the drilling process may be obtained by analysis of the volume of the drill cuttings removed from the well. For example, given a known drill bit size and rate of penetration, the expected volume of drill cuttings can be determined. A lower than expected volume of drill cuttings received at the surface may indicate inefficiency in the mud circulation process or premature deterioration of the cutting surfaces of the drill bit. Alternatively, a higher than expected volume of drill cuttings received at the surface may indicate that the hole is caving in or collapsing. As such, analysis of the volume of drill cuttings returned to the surface can be useful in optimizing drilling efficiency.

BRIEF DESCRIPTION OF THE DRAWINGS

For a more complete understanding of the features and advantages of the present disclosure, reference is now made to the detailed description along with the accompanying figures in which corresponding numerals in the different figures refer to corresponding parts and in which:

FIGS. 2A-2B are front and side views of a sensing device having an air curtain generator according to an embodiment of the present disclosure;

FIGS. 3A-3B are front and side views of a sensing device having an air curtain generator according to an embodiment of the present disclosure;

DETAILED DESCRIPTION

Figure 1:
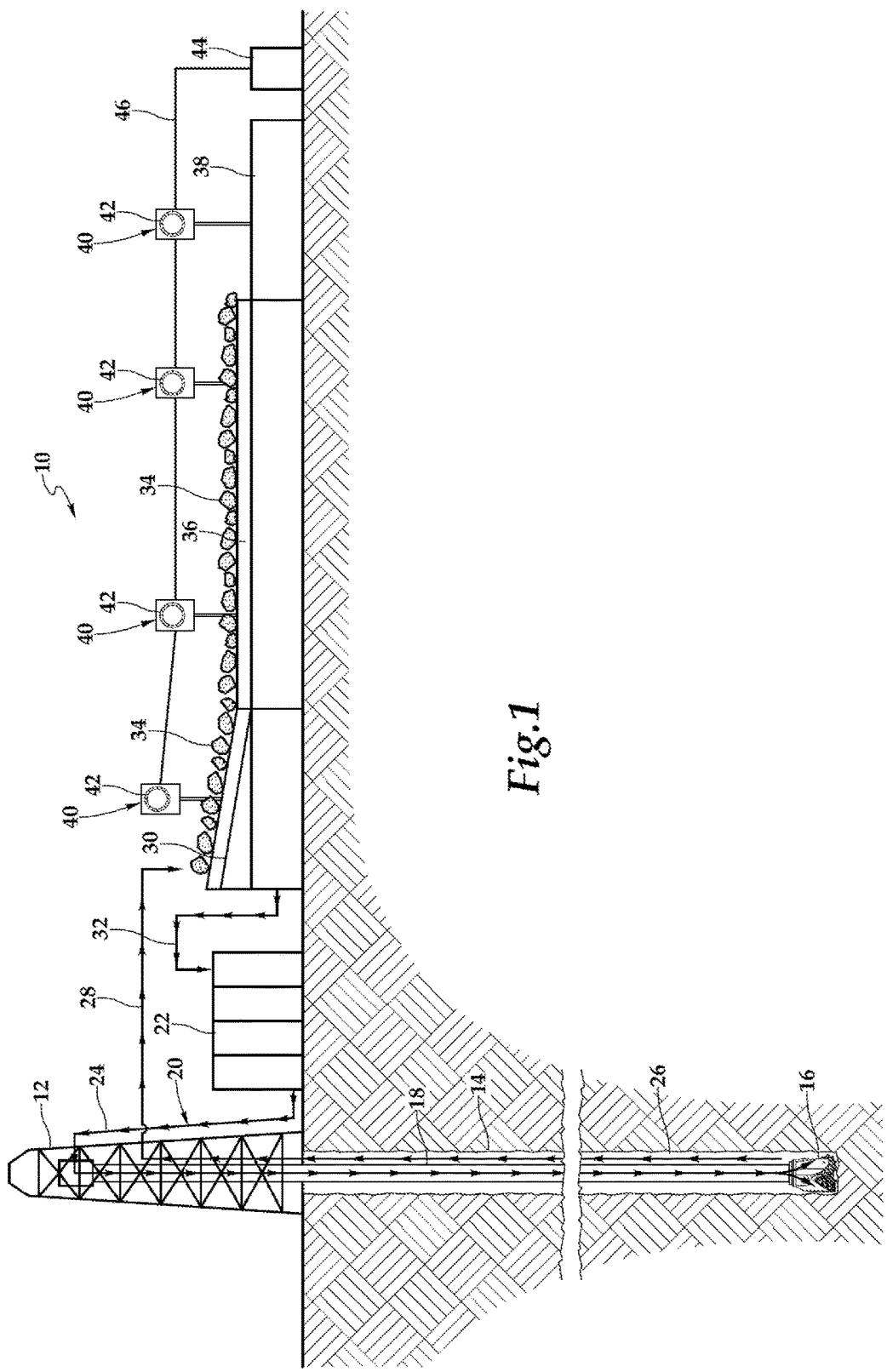
FIG. 1 is a schematic illustration of a well drilling operation including a plurality of sensing devices having air curtain generators according to an embodiment of the present disclosure.

While various system, method and other embodiments are discussed in detail below, it should be appreciated that the present disclosure provides many applicable inventive concepts, which can be embodied in a wide variety of specific contexts. The specific embodiments discussed herein are merely illustrative, and do not delimit the scope of the present disclosure.

In a first aspect, the present disclosure is directed to a sensing device. The sensing device includes an optical surface and an air curtain generator positioned around the optical surface. The air curtain generator has at least one nozzle that is operable to provide a continuous forced air region traveling away from the optical surface, thereby forming an air curtain around the optical surface.

In one embodiment, the optical surface may be a part of a lens. In another embodiment, the optical surface may be a part of a light source. In certain embodiments, the air curtain generator may have a plurality of nozzles. In some of these embodiments, the nozzles may be directed toward a focal point or a focal line. In one embodiment, the air curtain may be a conical air curtain. In some embodiments, the air curtain may be a rotating air curtain.

In a second aspect, the present disclosure is directed to a sensing device. The sensing device includes an optical surface, a first air curtain generator and a second air curtain generator. The first air curtain generator is positioned around the optical surface. The first air curtain generator has at least one nozzle that is operable to provide a continuous forced air region traveling away from the optical surface, thereby forming a first air curtain around the optical surface. The second air curtain generator is positioned around the first air curtain generator. The second air curtain generator has at least one nozzle that is operable to provide a continuous forced air region traveling away from the optical surface, thereby forming a second air curtain around the optical surface.

In one embodiment, the first air curtain generator may have a plurality of nozzles directed toward a first focal point and the second air curtain generator may have a plurality of nozzles directed toward the first focal point or a second focal point. In another embodiment, the first air curtain generator may have a plurality of nozzles directed toward a focal point and the second air curtain generator may have a plurality of nozzles directed toward a focal line. In a further embodiment, the first air curtain may be an air curtain rotating in a first direction and the second air curtain may be an air curtain rotating in the first direction or a second direction. In an additional embodiment, the first air curtain may be a rotating air curtain having a first angular velocity and the second air curtain may be a rotating air curtain having the first angular velocity or a second angular velocity.

In a third aspect, the present disclosure is directed to a method of protecting an optical surface of a sensing device. The method includes positioning an air curtain generator around the optical surface, the air curtain generator having at least one nozzle and discharging air through the at least one nozzle to provide a continuous forced air region traveling away from the optical surface, thereby forming an air curtain around the optical surface.

The method may also include directing the air toward a focal point, directing the air toward a focal line and/or generating a rotating air curtain. The method may further include positioning a second air curtain generator around the optical surface, the second air curtain generator having at least one nozzle and discharging air through the at least one nozzle of the second air curtain generator to provide a continuous forced air region traveling away from the optical surface, thereby forming a second air curtain around the optical surface.

FIG. 1 is a schematic illustration of an example of a well drilling operation 10 including a plurality of sensing devices having air curtain generators. Well drilling operation 10 includes a drilling rig 12 that is being used to drill a wellbore 14 through the various earth strata by rotating a drill bit 16 on the lower end of a drill string 18. During the drilling operation, a drilling fluid referred to herein as mud is being circulated through a closed loop 20 including mud tank 22 having a mud pump (not shown), a fluid pathway 24, drill string 18, drill bit 16, a well annulus 26, a fluid pathway 28, an inclined shaker 30 having a mud pump (not shown) and a fluid pathway 32. As illustrated, drill cuttings 34 are separated from the mud using inclined shaker 30. Drill cuttings 34 progress down inclined shaker 30 to a conveyer system 36 and then to a temporary storage container 38 for subsequent disposal. Along the path traveled by drill cuttings 34, well drilling operation 10 includes one or more sensing devices 40 having air curtain generators 42.

Sensing devices 40 may be used to determine the volume of drill cuttings 34 that is being received at the surface. The determined volume of drill cuttings 34 may be compared to an expected volume of drill cuttings to optimize drilling efficiency. In one example, sensing devices 40 may be optical sensing devices such as still cameras, video cameras, UV sensors/cameras, IR sensors/cameras, X-ray sensors/cameras, radar sensors, laser sensors, vision sensors, photoelectric sensors, optical analyzers including integrated computational elements, reflective devices including mirrors or the like that may be in communication with computer processing equipment operable to estimate the volume of drill cuttings 34 based upon the optical information obtained by sensing devices 40. In addition, certain of the sensing devices 40 may serve as light sources for other of the sensing devices 40 such that drill cuttings volume may be determined during drilling operations performed at night, for example. Alternatively or additionally, other types of sensors, such as ultrasonic sensors or level sensors may include air curtain generators 42. Due to the environment of well drilling operation 10 such as mud splatter, rain, mist, vapors, insects, particulate or other debris, sensing devices 40 each include an air curtain generator 42. In the illustrated embodiment, air curtain generators 42 are each connected to a common pressurized air source 44 via an air conduit 46. Alternatively, air curtain generators 42 may each have a dedicated pressurized air source, which may be contained within or located proximate to each sensing device 40. As explained in detail below, each air curtain generator 42 is operable to create a debris barrier in the form of an air curtain that surrounds an optical surface, such as a lens, of sensing device 40 and provides a continuous forced air region traveling away from the optical surface of sensing device 40 to prevent or minimize debris contact with the optical surface, which could degrade the sensing or measuring function of sensing device 40. As such, air curtain generators 42 improve sensor reliability, reduce maintenance time and expense and reduce wear on the optical surface of sensing device 40, thereby increasing sensor life. In addition, use of air curtain generators 42 in remote sensor applications, makes automated measurements and control more practical, thereby increasing the viability of such automated systems. Further, use of air curtain generators 42 may enhance personnel safety by reducing the time personnel are required in potentially hazardous areas.

Referring next to FIGS. 2A-2B, sensing device 50 includes a housing 52 formed from metal, plastic or other material suitable for the environment in which sensing device 50 will be operated. Housing 52 is operable to support and protect various component disposed therein used in the sensing operation. For example, housing 52 may contain one or more optical sensing devices such as still cameras, video cameras, UV sensors/cameras, IR sensors/cameras, X-ray sensors/cameras, radar sensors, laser sensors, vision sensors, photoelectric sensors, optical analyzers including integrated computational elements, reflective devices including mirrors or the like. In addition, housing 52 may contain various control subsystems such as a computer control subsystem including various blocks, modules, elements, components, methods or algorithms, that can be implemented using computer hardware, software, combinations thereof and the like. The computer hardware can include a processor configured to execute one or more sequences of instructions, programming stances or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network or any like suitable entity that can perform calculations or other manipulations of data. A machine-readable medium can take on many forms including, for example, non-volatile media, volatile media and transmission media. Non-volatile media can include, for example, optical and magnetic disks. Volatile media can include, for example, dynamic memory. Transmission media can include, for example, coaxial cables, wire, fiber optics and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM. Alternatively, some or all of the control systems may be located remote from sensing device 50 and communicated thereto via a wired or wireless communications protocol.

In the illustrated embodiment, sensing device 50 includes a sampling window 54 having an optical surface 56. Sampling window 54 may be made from a variety of transparent, rigid or semi-rigid materials that are configured to allow transmission of electromagnetic radiation, such as light, therethrough. For example, sampling window 54 may be made of, but is not limited to, glasses, plastics, semiconductors, crystalline materials, polycrystalline materials, hot or cold-pressed powders, combinations thereof or the like. Sampling window 54 may be a lens configured to receive electromagnetic radiation, transmit electromagnetic radiation toward an object or both. The lens may be any type of optical device including, but not limited to, a normal lens, a Fresnel lens, a diffractive optical element, a mirror or any other device operable for transmission, reflection and/or refraction of electromagnetic radiation known to those skilled in art.

To protect optical surface 56 from environmental hazards such as mud splatter, rain, mist, vapors, insects, particulate or other debris, sensing device 50 includes an air curtain generator 58. Air curtain generator 58 may be connected to a remote pressurized air source as described above with reference to FIG. 1 or a pressurized air source internal to sensing device 50. In either case, air is discharged from air curtain generator 58 via a plurality of nozzles 60. In the illustrated embodiment, nozzles 60 are angled relative to an axis of sampling window 54 to generally direct the air toward a focal point 62 as indicated by dotted lines 64 and as best seen in FIG. 2B. Air curtain generator 58 thus forms a conical air curtain that provides a protective zone around optical surface 56. As illustrated, the air curtain created by air curtain generator 58 does not blow against optical surface 56 but instead provides a continuous forced air region traveling away from optical surface 56 such that any entrained debris is prevented from contacting optical surface 56. In this manner, air curtain generator 58 is operable to keep optical surface 56 free from particulates, liquid droplets, corrosive vapors and other debris.

Referring next to FIGS. 3A-3B, sensing device 100 includes a housing 102 formed from metal, plastic or other material suitable for the environment in which sensing device 100 will be operated. Housing 102 is operable to support and protect various component disposed therein used in the sensing operation. In the illustrated embodiment, sensing device 100 includes a sampling window 104 having an optical surface 106. To protect optical surface 106 from environmental hazards such as mud splatter, rain, mist, vapors, insects, particulate or other debris, sensing device 100 includes an air curtain generator 108. Air curtain generator 108 may be connected to a remote pressurized air source as described above with reference to FIG. 1 or a pressurized air source internal to sensing device 100. In either case, air is discharged from air curtain generator 108 via a plurality of nozzles 110. In the illustrated embodiment, nozzles 110 are angled relative to an axis of sampling window 104 to generally direct the air toward a focal point 112 as indicated by dotted lines 114 and as best seen in FIG. 3B. In addition, nozzles 110 are angled to create rotation of the air curtain as indicated by arrow 116 and as best seen in FIG. 3B. Air curtain generator 108 thus forms a rotating conical air curtain that provides a protective zone around optical surface 106. As illustrated, the air curtain created by air curtain generator 108 does not blow against optical surface 106 but instead provides a continuous forced air region traveling away from optical surface 106 such that any entrained debris is prevented from contacting optical surface 106. In this manner, air curtain generator 108 is operable to keep optical surface 106 free from particulates, liquid droplets, corrosive vapors and other debris.

Figure 4:
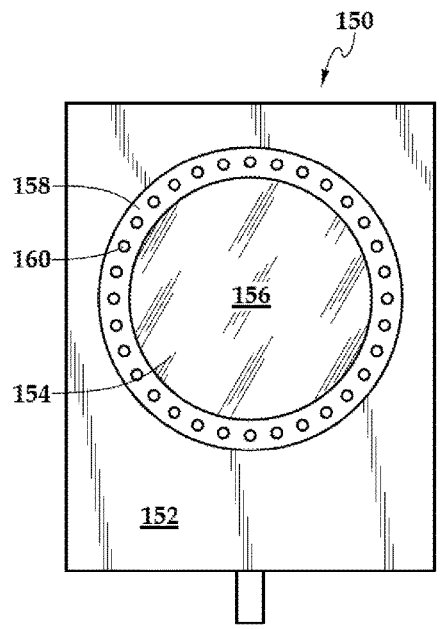
FIG. 4 is a front view of a sensing device having an air curtain generator according to an embodiment of the present disclosure.

Even though air curtain generators 58 and 108 have been depicted as having a particular number of nozzles, those skilled in the art should understand that air curtain generators having other numbers of nozzles are possible and are considered within the scope of the present disclosure. For example, referring next to FIG. 4, sensing device 150 includes a housing 152 formed from metal, plastic or other material suitable for the environment in which sensing device 150 will be operated. Housing 152 is operable to support and protect various component disposed therein used in the sensing operation. In the illustrated embodiment, sensing device 150 includes a sampling window 154 having an optical surface 156. To protect optical surface 156 from environmental hazards such as mud splatter, rain, mist, vapors, insects, particulate or other debris, sensing device 150 includes an air curtain generator 158. Air curtain generator 158 may be connected to a remote pressurized air source as described above with reference to FIG. 1 or a pressurized air source internal to sensing device 150. In either case, air is discharged from air curtain generator 158 via a plurality of nozzles 160. In the illustrated embodiment, nozzles 160 are more densely arranged than nozzles 60, 110 depicted above. As described above, nozzles 160 may be angled to generally direct air toward a focal point, may be angled to create rotation of the air curtain or both. As illustrated, the air curtain created by air curtain generator 158 does not blow against optical surface 156 but instead provides a continuous forced air region traveling away from optical surface 156 such that any entrained debris is prevented from contacting optical surface 156. In this manner, air curtain generator 158 is operable to keep optical surface 156 free from particulates, liquid droplets, corrosive vapors and other debris.

Figure 5:
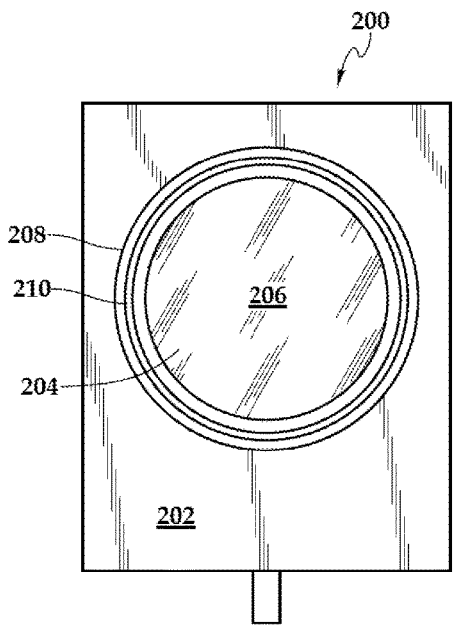
FIG. 5 is a front view of a sensing device having an air curtain generator according to an embodiment of the present disclosure.

As another example, referring next to FIG. 5, sensing device 200 includes a housing 202 formed from metal, plastic or other material suitable for the environment in which sensing device 200 will be operated. Housing 202 is operable to support and protect various component disposed therein used in the sensing operation. In the illustrated embodiment, sensing device 200 includes a sampling window 204 having an optical surface 206. To protect optical surface 206 from environmental hazards such as mud splatter, rain, mist, vapors, insects, particulate or other debris, sensing device 200 includes an air curtain generator 208. Air curtain generator 208 may be connected to a remote pressurized air source as described above with reference to FIG. 1 or a pressurized air source internal to sensing device 200. In either case, air is discharged from air curtain generator 208 via a single nozzle depicted as slot 210 that may be angled to generally direct air toward a focal point. As illustrated, the air curtain created by air curtain generator 208 does not blow against optical surface 206 but instead provides a continuous forced air region traveling away from optical surface 206 such that any entrained debris is prevented from contacting optical surface 206. In this manner, air curtain generator 208 is operable to keep optical surface 206 free from particulates, liquid droplets, corrosive vapors and other debris.

Figure 6:
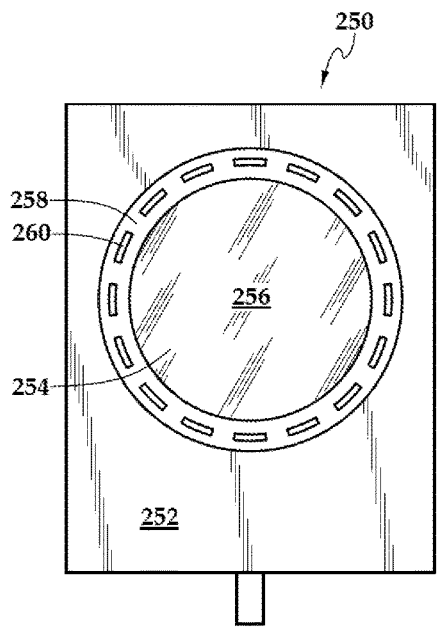
FIG. 6 is a front view of a sensing device having an air curtain generator according to an embodiment of the present disclosure.

Even though air curtain generators 58, 108 and 158 have been depicted as having nozzles of a particular design, those skilled in the art should understand that air curtain generators having nozzles with alternate designs are possible and are considered within the scope of the present disclosure. For example, referring next to FIG. 6, sensing device 250 includes a housing 252 formed from metal, plastic or other material suitable for the environment in which sensing device 250 will be operated. Housing 252 is operable to support and protect various components disposed therein used in the sensing operation. In the illustrated embodiment, sensing device 250 includes a sampling window 254 having an optical surface 256. To protect optical surface 256 from environmental hazards such as mud splatter, rain, mist, vapors, insects, particulate or other debris, sensing device 250 includes an air curtain generator 258. Air curtain generator 258 may be connected to a remote pressurized air source as described above with reference to FIG. 1 or a pressurized air source internal to sensing device 250. In either case, air is discharged from air curtain generator 258 via a plurality of nozzles 260. Unlike nozzles 60, 110, 160 above which were depicted as being round, nozzles 260 are depicted as rectangular and/or arched shaped slots. As described above, nozzles 260 may be angled to generally direct air toward a focal point, may be angled to create rotation of the air curtain or both. As illustrated, the air curtain created by air curtain generator 258 does not blow against optical surface 256 but instead provides a continuous forced air region traveling away from optical surface 256 such that any entrained debris is prevented from contacting optical surface 256. In this manner, air curtain generator 258 is operable to keep optical surface 256 free from particulates, liquid droplets, corrosive vapors and other debris.

Figure 7:
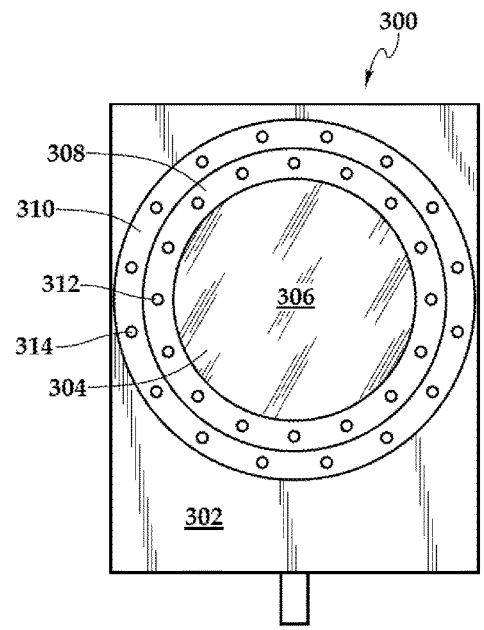
FIG. 7 is a front view of a sensing device having an air curtain generator according to an embodiment of the present disclosure.

Referring next to FIG. 7, sensing device 300 includes a housing 302 formed from metal, plastic or other material suitable for the environment in which sensing device 300 will be operated. Housing 302 is operable to support and protect various components disposed therein used in the sensing operation. In the illustrated embodiment, sensing device 300 includes a sampling window 304 having an optical surface 306. To protect optical surface 306 from environmental hazards such as mud splatter, rain, mist, vapors, insects, particulate or other debris, sensing device 300 includes an air curtain generator 308 and an air curtain generator 310. Air curtain generators 308, 310 may be connected to a remote pressurized air source as described above with reference to FIG. 1 or a pressurized air source internal to sensing device 300. In either case, air is discharged from air curtain generator 308 via a plurality of nozzles 312 that may be angled to generally direct air toward a focal point, may be angled to create rotation of the air curtain or both. Likewise, air is discharged from air curtain generator 310 via a plurality of nozzles 314 that may be angled to generally direct air toward a focal point, may be angled to create rotation of the air curtain or both. In this embodiment, the focal point for air from air curtain generators 308, 310 may be the same or different, the direction of rotation of the air curtain from air curtain generators 308, 310 may be the same or different and the angular velocity of rotation of the air curtain from air curtain generators 308, 310 may be the same or different. As illustrated, the air curtains created by air curtain generators 308, 310 do not blow against optical surface 306 but instead provides a continuous forced air region traveling away from optical surface 306 such that any entrained debris is prevented from contacting optical surface 306. In this manner, air curtain generators 308, 310 are operable to keep optical surface 306 free from particulates, liquid droplets, corrosive vapors and other debris.

Figure 8:
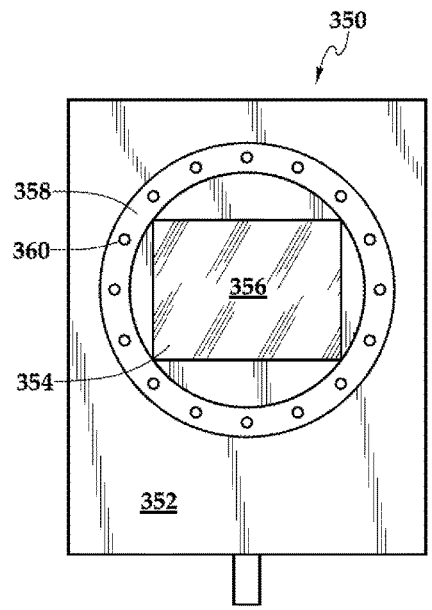
FIG. 8 is a front view of a sensing device having an air curtain generator according to an embodiment of the present disclosure.

Even though the air curtain generators and optical surfaces have been depicted as having the same shape, those skilled in the art should understand that air curtain generators and optical surfaces with alternate designs are possible and are considered within the scope of the present disclosure. For example, referring next to FIG. 8, sensing device 350 includes a housing 352 formed from metal, plastic or other material suitable for the environment in which sensing device 350 will be operated. Housing 352 is operable to support and protect various component disposed therein used in the sensing operation. In the illustrated embodiment, sensing device 350 includes a sampling window 354 having an optical surface 356 having a rectangular shape. To protect optical surface 356 from environmental hazards such as mud splatter, rain, mist, vapors, insects, particulate or other debris, sensing device 350 includes an air curtain generator 358 having a circular shape. Air curtain generator 358 may be connected to a remote pressurized air source as described above with reference to FIG. 1 or a pressurized air source internal to sensing device 350. In either case, air is discharged from air curtain generator 358 via a plurality of nozzles 360 that may be angled to generally direct air toward a focal point, may be angled to create rotation of the air curtain or both. As illustrated, the air curtain created by air curtain generator 358 does not blow against optical surface 356 but instead provides a continuous forced air region traveling away from optical surface 356 such that any entrained debris is prevented from contacting optical surface 356. In this manner, air curtain generator 358 is operable to keep optical surface 356 free from particulates, liquid droplets, corrosive vapors and other debris.

Figure 9:
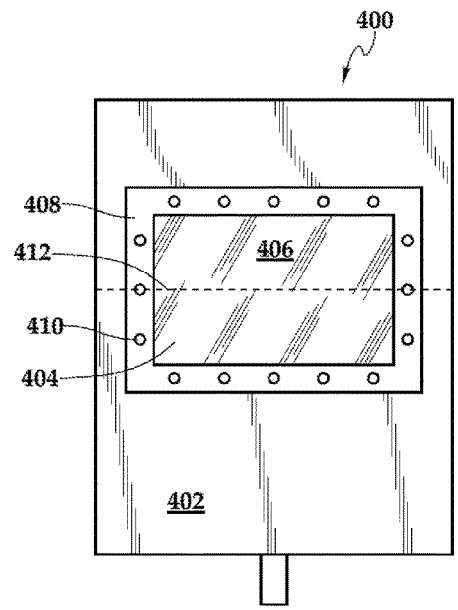
FIG. 9 is a front view of a sensing device having an air curtain generator according to an embodiment of the present disclosure.

Even though the air curtain generators have been depicted as having a particular shape, those skilled in the art should understand that air curtain generators with alternate designs are possible and are considered within the scope of the present disclosure. For example, referring next to FIG. 9, sensing device 400 includes a housing 402 formed from metal, plastic or other material suitable for the environment in which sensing device 400 will be operated. Housing 402 is operable to support and protect various component disposed therein used in the sensing operation. In the illustrated embodiment, sensing device 400 includes a sampling window 404 having an optical surface 406 that is rectangular. To protect optical surface 406 from environmental hazards such as mud splatter, rain, mist, vapors, insects, particulate or other debris, sensing device 400 includes an air curtain generator 408 that is rectangular. Air curtain generator 408 may be connected to a remote pressurized air source as described above with reference to FIG. 1 or a pressurized air source internal to sensing device 400. In either case, air is discharged from air curtain generator 408 via a plurality of nozzles 410 that may be angled to generally direct air toward a focal point or may be angled to generally direct air toward a focal line indicated as dashed line 412 located in front of optical surface 406 in a manner similar to focal point 62 being located in front of optical surface 56 in FIG. 2B. As illustrated, the air curtain created by air curtain generator 408 does not blow against optical surface 406 but instead provides a continuous forced air region traveling away from optical surface 406 such that any entrained debris is prevented from contacting optical surface 406. In this manner, air curtain generator 408 is operable to keep optical surface 406 free from particulates, liquid droplets, corrosive vapors and other debris.

Figure 10:
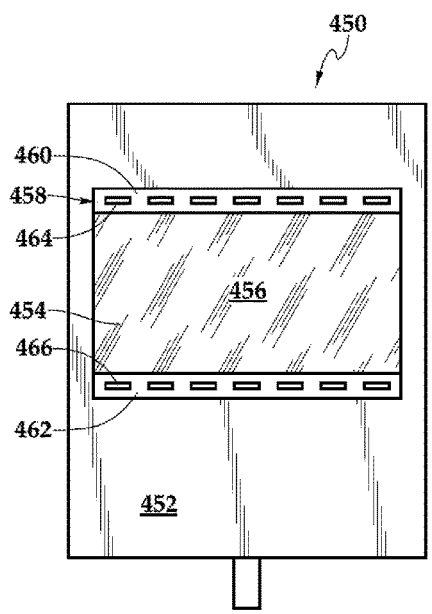
FIG. 10 is a front view of a sensing device having an air curtain generator according to an embodiment of the present disclosure.

Even though the air curtain generators have been depicted as having a continuous configuration, those skilled in the art should understand that air curtain generators having a discontinuous configuration are possible and are considered within the scope of the present disclosure. For example, referring next to FIG. 10, sensing device 450 includes a housing 452 formed from metal, plastic or other material suitable for the environment in which sensing device 450 will be operated. Housing 452 is operable to support and protect various component disposed therein used in the sensing operation. In the illustrated embodiment, sensing device 450 includes a sampling window 454 having an optical surface 456 having a rectangular shape. To protect optical surface 456 from environmental hazards such as mud splatter, rain, mist, vapors, insects, particulate or other debris, sensing device 450 includes an air curtain generator 458 having an upper element 460 and a lower element 462. Air curtain generator 458 may be connected to a remote pressurized air source as described above with reference to FIG. 1 or a pressurized air source internal to sensing device 450. In either case, air is discharged from air curtain generator 458 via a plurality of nozzles 464 of upper element 460 and a plurality of nozzles 466 of lower element 462 that may be angled to direct air toward a focal line. As illustrated, the air curtain created by air curtain generator 458 does not blow against optical surface 456 but instead provides a continuous forced air region traveling away from optical surface 456 such that any entrained debris is prevented from contacting optical surface 456. In this manner, air curtain generator 458 is operable to keep optical surface 456 free from particulates, liquid droplets, corrosive vapors and other debris.

Figure 11:
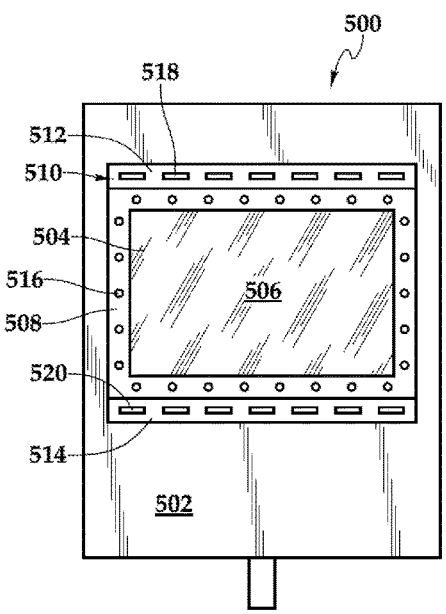
FIG. 11 is a front view of a sensing device having an air curtain generator according to an embodiment of the present disclosure.

Referring next to FIG. 11, sensing device 500 includes a housing 502 formed from metal, plastic or other material suitable for the environment in which sensing device 500 will be operated. Housing 502 is operable to support and protect various component disposed therein used in the sensing operation. In the illustrated embodiment, sensing device 500 includes a sampling window 504 having an optical surface 506. To protect optical surface 506 from environmental hazards such as mud splatter, rain, mist, vapors, insects, particulate or other debris, sensing device 500 includes an air curtain generator 508 and an air curtain generator 510 that includes upper element 512 and lower element 514. Air curtain generators 508, 510 may be connected to a remote pressurized air source as described above with reference to FIG. 1 or a pressurized air source internal to sensing device 500. In either case, air is discharged from air curtain generator 508 via a plurality of nozzles 516 that may be angled to generally direct air toward a focal point or focal line. Likewise, air is discharged from air curtain generator 510 via a plurality of nozzles 518 of upper element 512 and a plurality of nozzles 520 of lower element 514 that may be angled to generally direct air toward a focal line. As illustrated, the air curtains created by air curtain generators 508, 510 do not blow against optical surface 506 but instead provides a continuous forced air region traveling away from optical surface 506 such that any entrained debris is prevented from contacting optical surface 506. In this manner, air curtain generators 508, 510 are operable to keep optical surface 506 free from particulates, liquid droplets, corrosive vapors and other debris.

It should be understood by those skilled in the art that the illustrative embodiments described herein are not intended to be construed in a limiting sense. Various modifications and combinations of the illustrative embodiments as well as other embodiments will be apparent to persons skilled in the art upon reference to this disclosure. It is, therefore, intended that the appended claims encompass any such modifications or embodiments.

What is claimed is:

1. A sensing device for use in a wellbore operation, comprising:
    a sensor selected from the group consisting of IR sensors, X-ray sensors, radar sensors, laser sensors, photoelectric sensors, ultrasonic sensors, optical analyzers, and integrated computational elements for obtaining optical information;
    computer processing equipment in communication with the sensor and operable to estimate a volume of drill cuttings based upon the optical information; and
    an air curtain generator positioned around an optical surface, the air curtain generator having at least one nozzle operable to provide a continuous forced air region traveling away from the optical surface, thereby forming an air curtain around the optical surface to prevent or minimize debris from degrading the sensing or measuring function of the sensor, and thereby rotating the air curtain generator relative to the optical surface.

2. The sensing device as recited in claim 1 wherein the optical surface is part of a lens.

3. The sensing device as recited in claim 1 wherein the optical surface is part of a light source.

4. The sensing device as recited in claim 1 wherein the at least one nozzle further comprises a plurality of nozzles.

5. The sensing device as recited in claim 4 wherein the nozzles are directed toward a focal point.

6. The sensing device as recited in claim 1 wherein the air curtain further comprises a conical air curtain.

7. The sensing device as recited in claim 1 wherein the air curtain rotates with the air curtain generator.

8. A sensing device for use in a wellbore operation, comprising:
    an optical surface for obtaining optical information;
    computer processing equipment in communication with the optical surface and operable to estimate a volume of drill cuttings based upon the optical information;
    a first air curtain generator positioned around the optical surface, the first air curtain generator having at least one nozzle operable to provide a continuous forced air region traveling away from the optical surface, thereby forming a first air curtain around the optical, and thereby rotating the first air curtain generator relative to the optical surface; and
    a second air curtain generator positioned around the first air curtain generator, the second air curtain generator having at least one nozzle operable to provide a continuous forced air region traveling away from the optical surface, thereby forming a second air curtain around the optical surface;
    wherein the first and second air curtains prevent or minimize debris contact with the optical surface which could degrade a sensing or measuring function of the sensing device, thereby allowing the sensing device to determine a volume of drill cuttings.

9. The sensing device as recited in claim 8 wherein the optical surface is part of a lens.

10. The sensing device as recited in claim 8 wherein the optical surface is part of a light source.

11. The sensing device as recited in claim 8 wherein the first air curtain generator further comprises a plurality of nozzles directed toward a first focal point and wherein the second air curtain generator further comprises a plurality of nozzles directed toward a second focal point.

12. The sensing device as recited in claim 8 wherein the first air curtain rotates with the first air curtain generator.

13. The sensing device as recited in claim 8 wherein the first air curtain further comprises an air curtain rotating in a first direction and wherein the second air curtain further comprises an air curtain rotating in a second direction.

14. The sensing device as recited in claim 8 wherein the first air curtain further comprises a rotating air curtain having a first angular velocity and wherein the second air curtain further comprises a rotating air curtain having a second angular velocity.

15. A method of protecting an optical surface of a sensing device during the determination of a volume of dill cuttings received from a wellbore, comprising:
    positioning an air curtain generator around the optical surface, the air curtain generator having at least one nozzle;
    rotating the air curtain generator relative to the optical surface by discharging air through the at least one nozzle to provide a continuous forced air region traveling away from the optical surface and to form an air curtain around the optical surface to prevent or minimize debris contact with the optical surface, which could degrade a sensing or measuring function of the sensing device; and
    determining the volume of drill cuttings.

16. The method as recited in claim 15 wherein discharging air through the at least one nozzle further comprising directing the air toward a focal point.

17. The method as recited in claim 15 wherein the air curtain rotates with the air curtain generator.

18. The method as recited in claim 15 further comprising:
    positioning a second air curtain generator around the optical surface, the second air curtain generator having at least one nozzle; and
    discharging air through the at least one nozzle of the second air curtain generator to provide a continuous forced air region traveling away from the optical surface, thereby forming a second air curtain around the optical surface.

19. The method as recited in claim 18 wherein discharging air through the at least one nozzle of the second air curtain generator causes the second air curtain generator to rotate relative to the optical surface.

* * * * *